United States Patent
Wei

(10) Patent No.: US 9,612,186 B2
(45) Date of Patent: Apr. 4, 2017

(54) DEVICE AND METHOD FOR OPTICALLY DETERMINING PARTICLE PROPERTIES

(71) Applicant: OLYMPUS SOFT IMAGING SOLUTIONS GMBH, Muenster (DE)

(72) Inventor: Yi Wei, Muenster (DE)

(73) Assignee: OLYMPUS SOFT IMAGING SOLUTIONS GMBH, Muenster (DE)

( * ) Notice: Subject to any disclaimer, the term of this patent is extended or adjusted under 35 U.S.C. 154(b) by 0 days.

(21) Appl. No.: 15/079,627

(22) Filed: Mar. 24, 2016

(65) Prior Publication Data

US 2016/0202165 A1 Jul. 14, 2016

Related U.S. Application Data

(63) Continuation of application No. PCT/EP2014/002440, filed on Sep. 10, 2014.

(30) Foreign Application Priority Data

Sep. 24, 2013 (DE) .................. 10 2013 219 181

(51) Int. Cl.
*G01N 15/02* (2006.01)
*G01J 4/00* (2006.01)
(Continued)

(52) U.S. Cl.
CPC ..... *G01N 15/0227* (2013.01); *G01N 15/1434* (2013.01); *G02B 21/0092* (2013.01); *G02B 21/082* (2013.01); *G02B 27/1006* (2013.01); *G02B 27/288* (2013.01); *G01N 2015/1465* (2013.01); *G01N 2021/217* (2013.01); *G02B 5/20* (2013.01); *G02B 5/30* (2013.01)

(58) Field of Classification Search
CPC ............ G01N 15/02; G01N 21/00; G01J 4/00
USPC ........................................ 356/336
See application file for complete search history.

(56) References Cited

U.S. PATENT DOCUMENTS 4,666,245 A 5/1987 Pointer
6,867,919 B2 3/2005 Seyfried
(Continued)

FOREIGN PATENT DOCUMENTS

DE 3341302 A1 5/1985
DE 10052384 A1 5/2002
(Continued)

OTHER PUBLICATIONS

International Search Report dated Dec. 9, 2014 issued in PCT/EP2014/002440.

*Primary Examiner* — Roy M Punnoose
(74) *Attorney, Agent, or Firm* — Scully, Scott, Murphy & Presser, PC

(57) ABSTRACT

A device, a method and a system for optically determining particle properties, in particular size and reflectivity. The device includes at least one light source assembly having at least one light source, a polarizer assembly, at least one sample holder—which can be illuminated by the least one light source assembly—for accommodating particle preparations to be investigated, at least one analyzer assembly, and at least one imaging device with at least one color-resolving matrix image sensor. The device is designed to guide light reflected by a particle preparation and having a color-coded polarization to the at least one matrix image sensor.

25 Claims, 3 Drawing Sheets

(51) Int. Cl.
*G01N 15/14* (2006.01)
*G02B 21/00* (2006.01)
*G02B 21/08* (2006.01)
*G02B 27/10* (2006.01)
*G02B 27/28* (2006.01)
*G02B 5/20* (2006.01)
*G02B 5/30* (2006.01)
*G01N 21/21* (2006.01)

(56) References Cited

U.S. PATENT DOCUMENTS

| | | | |
|---|---|---|---|
| 7,298,551 | B2 | 11/2007 | Wolleschensky |
| 7,660,036 | B2 | 2/2010 | Metzger |
| 7,701,632 | B2 | 4/2010 | Wolleschensky |
| 8,422,003 | B2 | 4/2013 | Hartrumpf et al. |
| 8,675,195 | B2 | 3/2014 | Ihlefeld et al. |
| 2004/0238361 | A1* | 12/2004 | Shulman ............... G01N 21/21 204/452 |
| 2006/0011857 | A1 | 1/2006 | Funk et al. |
| 2009/0046360 | A1 | 2/2009 | Funk et al. |
| 2010/0141950 | A1 | 6/2010 | Katsunuma |
| 2010/0282945 | A1* | 11/2010 | Yokogawa ........ H01L 27/14621 250/208.1 |

FOREIGN PATENT DOCUMENTS

| | | |
|---|---|---|
| DE | 102005062439 B3 | 5/2007 |
| DE | 202007014466 U1 | 2/2008 |
| DE | 102009014080 A1 | 9/2010 |
| EP | 1396739 A1 | 3/2004 |
| EP | 1617253 A1 | 1/2006 |
| EP | 1914572 A1 | 4/2008 |
| EP | 2562513 A1 | 2/2013 |
| WO | WO 94/14049 A1 | 6/1994 |
| WO | WO 2006/091221 A2 | 8/2006 |

* cited by examiner

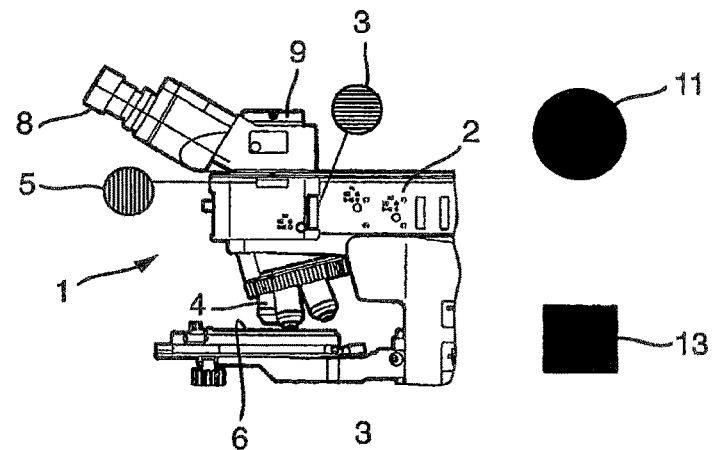
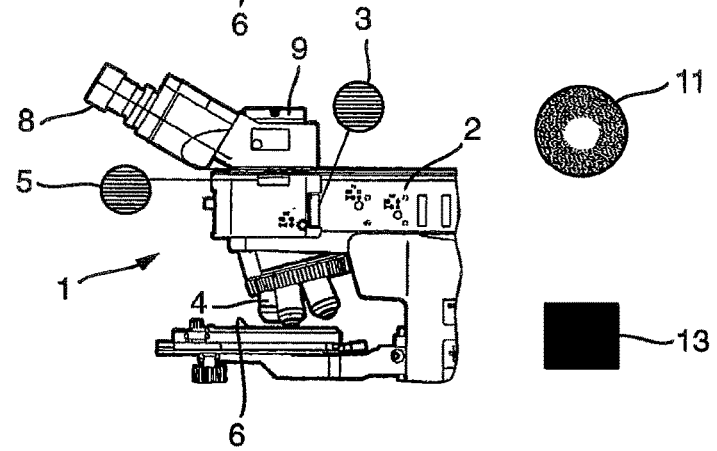
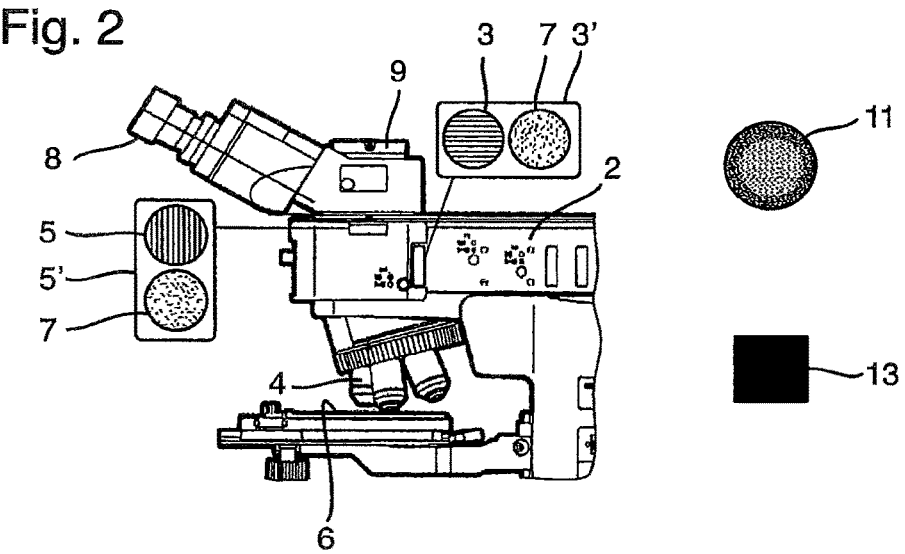

DEVICE AND METHOD FOR OPTICALLY DETERMINING PARTICLE PROPERTIES

CROSS-REFERENCE TO RELATED APPLICATIONS

This application is a continuation of PCT International Application No. PCT/EP2014/002440, filed on Sep. 10, 2014, and claims priority to German Patent Application No. DE 10 2013 219 181.2, filed on Sep. 24, 2013. The entire contents of PCT International Application No. PCT/EP2014/002440 and German Patent Application No. DE 10 2013 219 181.2 are incorporated herein by reference.

BACKGROUND

The invention relates to a device, a method and a system for optically determining particle properties, in particular size and reflectivity. The device comprises at least one light source assembly having at least one light source, a polarizer assembly, at least one sample holder—which can be illuminated by the at least one light source assembly—for accommodating particle preparations to be investigated, at least one analyzer assembly, and at least one imaging device with at least one color-resolving matrix image sensor.

The automatic measurement of particles with computer systems which are connected to an enlarging device is known. Particle properties such as shape, diameter and other geometric dimensions are detected by recording an image of the particles which is processed using a threshold detection method. This is normally done using so-called crossed polarized light. This means that the light is first linearly polarized by a polarizer in a polarization direction, and after being reflected by the particles to be investigated, is guided through an analyzer that has a linear polarization filter, the polarization direction, or respectively polarization plane, of which is at a 90° angle to the polarization plane, or respectively polarization direction, of the polarizer. This yields the best separation of particles from a bright background.

Other particle properties such as the reflectivity, or respectively reflection intensity, and hence the type of particles (metal or nonmetal) are detected by taking a second image using parallel polarized light, i.e., under imaging conditions in which the polarizer and analyzer are positioned parallel with respect to their polarization planes. Alternatively, the second image is taken without a polarizer with unpolarized light, and/or without an analyzer while retaining the effect.

The entire classification of the particles according to size and type hence requires two different images which are recorded under two different lighting conditions.

In the known method, the first image is typically recorded while the polarization directions of the polarizer and analyzer are perpendicular to each other, whereas the second image is recorded while the two are positioned parallel. The chronological sequence of the two images is unimportant. The shape and hence geometric dimensions of the particles are obtained from the image which was recorded with the crossed polarizer and analyzer, and the analysis of the second image with a parallel polarizer and analyzer reveals whether or not the particles are reflective by the brightness resulting at the location of the particles in this configuration.

Contrastingly, an object of the present invention is to accelerate and simplify the characterization of particles.

SUMMARY

This underlying objective is achieved with a device for optically determining particle properties, in particular the size and reflectivity, comprising at least one light source assembly having at least one light source, a polarizer assembly, at least one sample holder for receiving particle preparations to be analyzed that can be illuminated by the at least one light source assembly, at least one analyzer assembly, and at least one imaging device having at least one color-resolution matrix image sensor which is further developed in that the device is configured to direct light reflected by a particle preparation onto the at least one matrix image sensor by means of color-coded polarization.

In the context of the present disclosure, the "size" of particles is understood to be the geometric dimensions of the particle such as the length, diameter, surface and shape, etc.

A device according to an embodiment of the invention is for example a microscope, a macroscope, a stereo microscope, or a macroimaging station with observation under reflected light.

The device makes it possible to provide all the necessary information about the particles of the particle preparations using only a single RGB color image with an optical assembly which conducts reflected light from particles encoded with a specific code to an image sensor, and to this end, generates light with color-coded polarization to illuminate the particle preparations.

Embodiments of the invention, as described in this disclosure, are based on the underlying concept that a second image can be spared when the first and only image of the particles already contains all the information due to the light generated according to the invention and illuminating the particle preparation to identify both the particle size as well as the type of the particles. To this end, the light must comprise components of different polarizations in a distinguishable manner. This is accomplished according to the embodiments of the invention by means of color coding in that part of the color spectrum of the illuminating light is linearly polarized, and another part of the spectrum is linearly polarized in a different direction, or perhaps not polarized, or only partially polarized.

Since it is known which spectral components, i.e., which colors, have which polarization state based on the color coding, the particle sizes and reflectivity of the particles can simultaneously be deduced from the color information of the color- and spatially-resolved image.

Due to the measure according to the embodiments of the invention, the problem of shifts in the specimen relative to the optical components of the device is furthermore avoided, which leads to problems in identifying the particles when comparing the two images recorded according to the conventional method.

The light with color-coded polarization may have wavelength ranges in which the different states of polarization exist together. It is, however, necessary for there also to be wavelength ranges in which only one or the other polarization state predominates to enable separation in a subsequent image analysis. If such separate wavelength ranges did not exist, the light would also not have color-coded polarization.

In the device, the linear polarization filter of the analyzer is preferably positioned perpendicular to the polarization direction of a linearly polarized part of the light with color-coded polarization. This part is used to determine the geometric properties of the particles.

The device for color coding the polarization can be configured on the one hand to generate linearly polarized light of at least one first wavelength range in a first polarization direction and, on the other hand, to generate unpolarized light or polarized light with at least one polarization component in a second polarization direction different from the first polarization direction, in particular perpendicular to the first polarization, in at least one second wavelength range, wherein the first wavelength range(s) do not, or only partially, overlap with the second wavelength range(s).

In this context, the first polarization direction can be aligned perpendicular to a polarization direction of the analyzer.

A coding assembly can be included by means of which the color-coded polarization is generated, wherein the coding assembly is a part of the light source assembly, polarization assembly or analyzer assembly. The coding assembly comprises a plurality of optical elements in the optical path of the optical system before or in the polarizer, or also in conjunction with the analyzer, by means of which the polarization is color-coded.

In one embodiment, the coding assembly has a dichroic beam splitter which divides incident light into a first partial beam and a second partial beam with different wavelength ranges, wherein a linear polarizer is arranged in the optical path of the first partial beam, and a color filter is arranged in the optical path of the second partial beam, wherein the partial beams are combined into an outgoing light beam in a beam recombiner after passing through the polarizer or respectively the color filter. This coding assembly can be used to particular advantage in the polarization assembly.

When dichroic beam splitters are used, the wavelength spectrum can be divided into a plurality of sequential wavelength ranges which are alternatingly divided into the first and second partial beam. A color filter is arranged in the second partial beam, and it lets a limited wavelength range pass through, or only one wavelength in an extreme case. The color filter is selected such that it lets a wavelength range in the second partial beam pass through. It is unnecessary to use a polarizer in the second partial beam; however, this can be done supportively, wherein the polarizer is then preferably aligned perpendicular to the polarizer in the first partial beam.

The beam splitter is preferably designed as a dichroic beam splitter that in particular is arranged inverted to the first dichroic beam splitter with respect to optical path if applicable. The beam recombiner can also be a semitransparent mirror. In this disclosure, this means that the mirror lets light pass through coming at an angle from one side, and reflects light coming from another side.

In one likewise advantageous embodiment which can also be used in a particularly advantageous manner for the polarization assembly, the coding assembly has an arrangement, in the direction of incident light, consisting of a first lens, a first prism, a second prism and a second lens, wherein the incident light is spread out into a spectral band after passing through the first prism, wherein a combination filter with a polarizer and color filter is arranged at the location of the spectral band, by means of which a part of the spectral band is guided through the polarizer, and another part of the spectral band is guided through the color filter.

In this case, the spectral band of the incident light is divided overlap-free into two different ranges with the exception of a limited blurring of the spectrum, wherein one range is linearly polarized, and the other range passes through the color filter. This second range is hence restricted to the range which can pass through the color filter.

The color filter can be replaced by another transparent filter or a slit as long as the unpolarized light does not contain an essential spectral component which does not correspond to the color provided for the unpolarized light. Since the light is spectrally spread at this location, this arrangement corresponds to a color filter.

With respect to the combination filter, the second prism and second lens are preferably arranged inverted relative to the first prism and the first lens. In this manner, the spectral band is combined into a common, in particular parallel, light beam after passing through the combination filter, the light of the light beam having a color-coded polarization. In this case, part of the incident light has been filtered out by the color filter and is suppressed or does not exist in the color spectrum of the resulting light beam.

A likewise embodiment of the device is characterized in that the coding assembly has a combination filter with a pattern having a number of neighboring zones in a linear strip arrangement, a concentric arrangement, or an arrangement with radial strips, wherein polarizers and color filters alternate in neighboring zones. A corresponding combination filter with a pattern having a number of neighboring zones is used to generate different components of the light with color-coded polarization in its different zones. The zones should be fine enough to homogeneously illuminate the surface of the particle preparations for imaging purposes with both types of light. This embodiment of the coding assembly with a combination filter can be advantageously used both in a polarization assembly as well as alternatively in an analyzer assembly. When the combination filter is used in the polarization assembly, the polarization direction of the polarization component is selected to be perpendicular to the polarization direction of the analyzer; when used in the analyzer assembly, the polarization direction should be perpendicular to the polarizer.

The colored portion can be achieved by using a combination of a retardation plate, such as a $\lambda/2$ plate, also in combination with other retardation plates, and a color filter behind the polarizer.

The optimum result is achieved by a specific surface ratio between both parts in the combination filter, as well as a corresponding adjustment of the image analysis software. The surfaces of the polarization component and the color filter component preferably have a ratio of 1:1 to 10,000:1, in particular between 3:1 to 100:1.

The combination filter can have a central opening for an Abbé optical system of a stereo microscope. The combination filter then has an annular surface so that ideal homogenized illumination with both components of the color-coded polarized light is enabled with concentric zones, or respectively radially arranged zones.

In another embodiment of the device according to the invention, the coding assembly has one or more $\lambda$ plates that is/are designed to retain the polarization of linearly polarized light at a certain wavelength, and at least partially destroy the polarization at other wavelengths. The use of $\lambda$ plates of a full wavelength, or also of multiple wavelengths, exploits the fact that the optically-active materials rotate the polarization plane of polarized light. This effect is, however, dispersive so that the polarization planes can be rotated by different amounts for different wavelengths. For a certain wavelength, i.e., a certain color, there is a specific rotation of the linearly polarized light at 360°, whereas a different rotation occurs for other wavelengths. By combining a plurality of $\lambda$ plates, the polarization can be at least partially destroyed for these other wavelengths. An unpolarized component of the light is therefore present at the outlet in other wavelengths, whereas the linearly polarized light is still available at the selected wavelength. This coding assembly can be included in the polarization assembly or in the analyzer assembly. In the latter case, the coding assembly can assume the task of the analyzer to achieve the same effect.

Another embodiment contains at least two different light sources, wherein the light sources generate light with at least partially different colors or color spectra, wherein in particular one light source generates white light, and another light source generates colored light. In this case, the light of the first source can be polarized in the polarizer, whereas the colored light from the second light source can for example remain unpolarized. The color coding of the polarization of the light is easily achieved when there are two different light sources, of which only one illuminates the polarizer. The colored light can be also generated by a laser. At least one colored light source furthermore preferably comprises an external light source. This is the light source of the light that is not polarized in the polarizer.

In each of the described cases, the image evaluation takes into account the wavelength ranges in which the different polarizations are known, i.e., the known color coding of the light polarization.

The imaging device can have an image sensor with an upstream Bayer filter, three sensors with a beam splitter prism, and/or upstream color filters, or an X3 color sensor. Image sensors with Bayer filters are used in many applications including photography. For each pixel, or respectively each matrix cell of the sensor, the Bayer filter has a single-color filter which is either red, green or blue. At a pixel of a colored image, two color components which cannot be directly measured due to the color filter before the pixel, are usually interpolated from the pixel values of the adjacent pixels in front of which the color filter of the corresponding color is located. For each pixel, X3 sensors use three sensor elements which overlap in several layers to achieve all three primary colors with each pixel.

The underlying object of the invention is also achieved with a method for optically determining particle properties, in particular the size and reflectivity, wherein a particle preparation is placed in a sample holder of a device for optically determining particle properties, in particular an above-described device according to the invention, and a color and spatially resolved image of the particle preparation, or a part of the particle preparation, is made, which is further developed in that the particle preparation, or a part of the particle preparation, is illuminated using a reflected-light method, wherein light with color-coded polarization reflected by a particle preparation is conducted to at least one matrix image sensor.

The method has same properties, features and advantages as the above-described device.

The method can be further developed in that the light with color-coded polarization contains on the one hand linearly polarized light of at least one first wavelength range in a first polarization direction and, on the other hand, unpolarized light or polarized light with at least one polarization component in a second polarization direction different from the first polarization direction, in particular perpendicular to the first polarization, in at least one second wavelength range, wherein the first wavelength range(s) do not, or only partially, overlap with the second wavelength range(s).

The light reflected by the particle preparation can be conducted through an analyzer with a linear polarization filter, the polarization direction of which is aligned perpendicular to a first polarization direction of the light with color-coded polarization. Alternatively, the color coding of the polarization may also occur only after reflection, in that for example light linearly polarized in one direction, such as white light, is first shone on the sample, and then a division occurs in the analyzer assembly according to polarization and color, in particular as described above.

Size information is determined from the color- and spatially-resolved image information of a single image consisting of at least one wavelength range with a first polarization direction, and information on the reflectivity of particles of the particle preparation is determined from at least one second wavelength range with unpolarized light or with at least one polarization component in a second polarization direction different from the first polarization direction.

Within the scope of this disclosure, a wavelength range is understood to include an individual wavelength when light with only one wavelength, or a narrow band with a small bandwidth, is generated by a corresponding color filter, or a corresponding light source. Within the scope of the invention, light with at least partially different wavelengths and different polarization states is also generated by two different light sources and then mixed together to illuminate particle preparations.

The underlying object of the invention is also achieved by a system for optically determining particle properties, in particular size and reflectivity, with an above-described device according to the invention and an apparatus which has an interface connected to the device, a data memory and a processor for receiving, saving and processing color- and spatially resolved images, and which is further developed in that the evaluation apparatus is configured and set up using a computer program to determine size information from the color- and spatially-resolved image information of a single image consisting of at least one wavelength range with a first polarization direction, and to determine information on the reflectivity of particles of the particle preparation from at least one second wavelength range with unpolarized light or with at least one polarization component in a second polarization direction different from the first polarization direction.

The system also has the same advantages, features and properties as the device disclosed and the method disclosed.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general idea of the invention, using exemplary embodiments with reference to the drawings, whereby we expressly refer to the drawings with regard to all details according to the invention that are not explained in greater detail in the text.

In the figures:

FIGS. 1a and 1b show a schematic representation of a known device for detecting particle properties, FIG. 2 shows a schematic representation of a device according an embodiment of the invention.

In the drawings, the same or similar elements and/or parts are provided with the same reference numbers in order to prevent the item from needing to be reintroduced.

DETAILED DESCRIPTION

Figure 3:
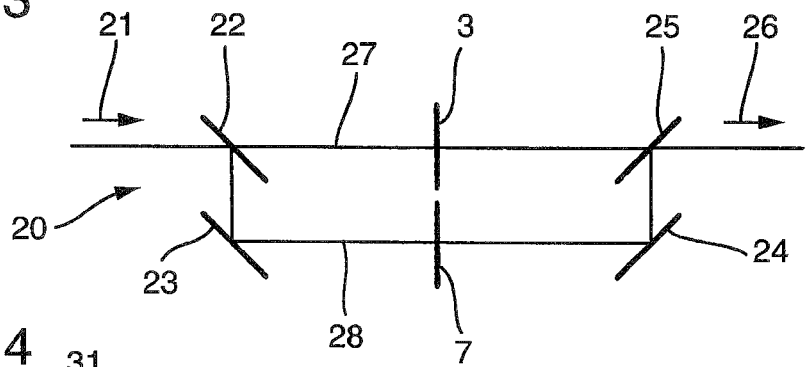
FIG. 3 shows a schematic representation of a coding assembly according to an embodiment of the invention.

Embodiments of the invention will be described below with reference to a reflected-light microscope. However, the embodiments are also readily transferable and applicable to other devices such as microscopes operated in a reflected-light method, macroscopes, stereo microscopes or macro-imaging stations.

FIGS. 1a) and b) schematically portray a section of a known reflected-light microscope 1 which can be used to determine particle properties. A reflected-light microscope means that the specimen is illuminated from the same side from which it is viewed with the lenses in contrast to transmitted light microscopy in which the specimen is transilluminated.

The reflected-light microscope 1 has a so-called light house 2 which has an illuminating system such as a lamp to illuminate a specimen on a specimen carrier 6. The optical path is not shown in FIGS. 1a) and 1b). The illuminating light is guided through a polarizer 3 in which it is linearly polarized. In FIG. 1a), this is a horizontal direction. The polarization direction is the same in FIG. 1a) and FIG. 1b). After passing through the polarizer 3, the illuminating light is deflected and directed to a specimen on the specimen carrier 6. This can be accomplished by a lens 4, as well as from the outside. The light reflected by the specimens on the specimen carrier 6 is conducted by a lens 4 to an analyzer 5 and then to an ocular 8 and simultaneously to an imaging device 9.

FIG. 1a) differs from FIG. 1b) in the polarization direction of the analyzer 5. In FIG. 1a), the analyzer 5 is positioned with a vertical polarization direction, i.e., perpendicular to the polarization direction of the polarizer 3; in FIG. 1b), the polarizer 3 and analyzer 5 are set up in parallel.

The right parts of FIG. 1a) and 1b) depict the visual appearances of reflective particles 11 and non-reflecting particles 13. In the case depicted as an example, the reflective particle 11 is round, and the non-reflecting particle 13 is rectangular. In the configuration depicted in FIG. 1a) with the crossed polarizer 3 and analyzer 5, both particles 11, 13 appear black such that the geometric properties of these particles can be ideally detected. In FIG. 1b), the polarizer 3 and analyzer 5 are parallel to each other. The reflective particle 11 appears brighter since reflected light passes through the analyzer 5 and hence creates a brighter image. In this manner, both the particle sizes and particle types are distinguishable in the two images which were made according to the configuration in FIG. 1a) and FIG. 1b).

FIG. 2 also depicts a reflected-light microscope 1 that differs from the reflected-light microscope 1 from FIG. 1 in terms of the type of light source assembly in the light house 2. According to FIG. 2, instead of only one linearly polarized polarizer 3, a modified polarizer assembly 3' is provided with a combination of a polarizer 3 and a color filter 7 for the light from the internal light source, alternatively also combined different light sources. The polarization filter for the analyzer 5 is configured perpendicular to the polarizer 3 of the polarizer assembly 3'. By means of the polarizer 3 and the color filter 7, light with color-coded polarization is generated in the light source assembly in the reflected-light microscope 1 which serves to illuminate the specimens on the specimen carrier 6.

The part of the wavelength spectrum which is polarized by the polarizer 3, together with the analyzer 5 arranged perpendicular thereto, produces the configuration from FIG. 1a) such that the geometric properties of particles are thereby measurable, whereas the part of the wavelength spectrum that passes through the color filter 7 is not correspondingly linearly polarized, and hence corresponds to the configuration from FIG. 1b) since at least one component of the polarization of this light is polarized parallel to the analyzer 5. This component is used to detect the particle type, i.e., whether or not the respective particle is reflective.

Alternatively, a modified analyzer assembly 5' with a combination consisting of a polarization filter of the analyzer 5 and a color filter 7 can also be used. In this case, the polarization assembly only contains one conventional polarizer, but no color filter. Furthermore in this case, the polarization directions of the polarization filter components in the polarizer 3 and analyzer 5 are perpendicular to each other.

FIG. 3 schematically portrays a first coding assembly 20 according to the invention for a reflected-light microscope 1 in which the incident light 21 enters from the left and contacts a dichroic beam splitter 22. This part of the incident light 21 is divided into two or more wavelength ranges which are divided on the one hand into a transmitted, first partial beam 27 and, on the other hand, into a reflected, second partial beam 28. The components reflected by the dichroic beam splitter 22 are again reflected by a mirror 23.

The first partial beam 27 is guided through a polarizer 3, whereas the second partial beam 28 is guided through a color filter 7. After passing through the color filter 7, the second partial beam 28 is deflected by a mirror 24 toward a beam recombiner 25 where it meets the first partial beam 27 and is combined therewith into an expanded light beam 26.

The beam recombiner 25 can be a dichroic beam divider that is arranged inverted, or a semitransparent mirror which is transparent on the side of the incoming first partial beam 27 and is designed to be reflective on the side of the incoming second partial beam.

Since dichroic beam dividers divide the wavelength spectrum into several ranges which are either reflected or pass through, the coding assembly 20 produces a spectrum with several ranges that are linearly polarized, and with at least one color-filtered wavelength range.

Figure 4:
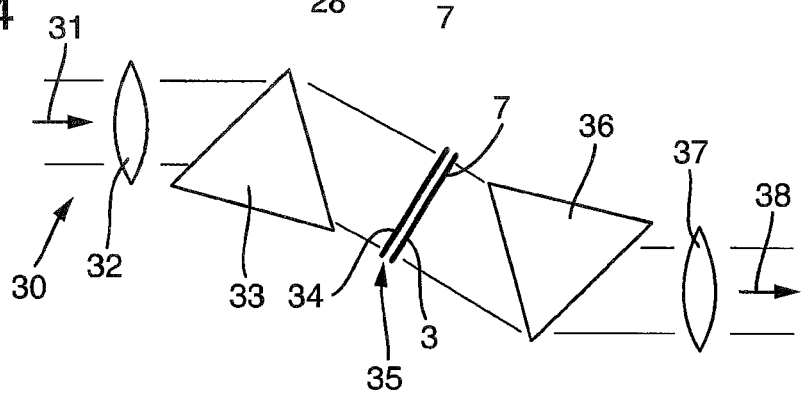
FIG. 4 shows a schematic representation of a another coding assembly according to an embodiment of the invention.

FIG. 4 shows an alternative example of a coding assembly 30. Incident parallel light 31 initially encounters a lens 32 which for example can be designed spherical or cylindrical. The first lens 32 bundles the incident light into a point or line. A prism 33 follows which spectrally divides the point or line to produce a spectral band 34. A combination filter 35 which linearly polarizes a large part of the spectral band 34 with a polarizer 3, and a color filter 7 which filters by color a smaller part of the spectral band 34, are arranged at the location of the spectral band 34.

This is followed by a second prism 36 and a second lens 37 which reverse the optical conversions of the incident light 31 in the first lens 32 and the first prism 33 such that a parallel light beam with color-coded polarization exits.

Figure 5:
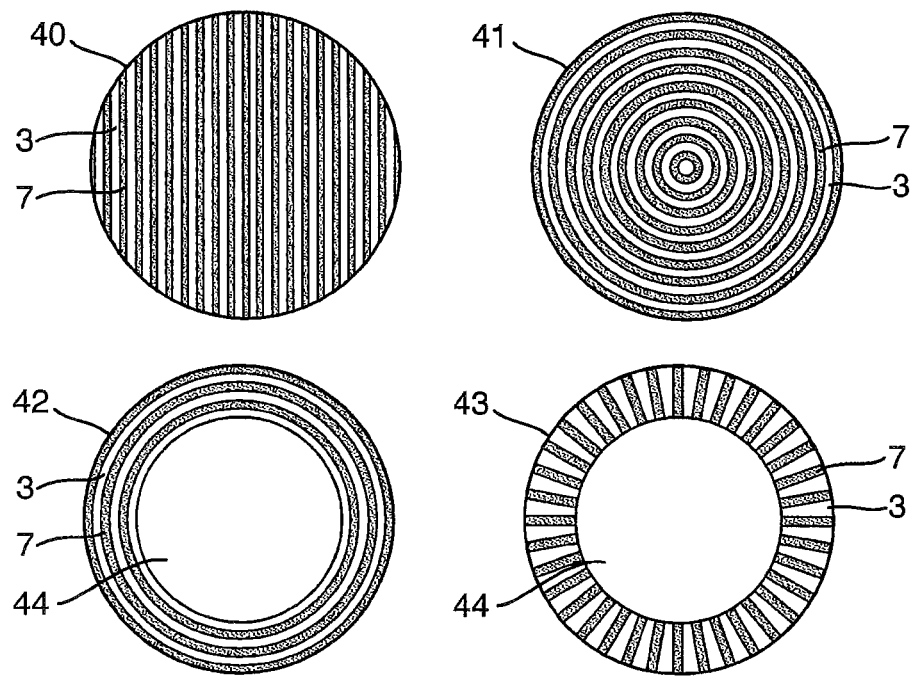
FIG. 5 shows a schematic representation of combination filters according to an embodiment of the invention.

FIG. 5 shows four examples of combination filters 40, 41, 42, 43 which have narrow zones with polarizer 3 and color filter 7 which alternate with each other from zone to zone, illustrated by lighter and darker areas.

To this end, the combination filter 40 has linear, strip-shaped areas, and the combination filter 41 has concentric zones. The combination filters 42 and 43 each have a central opening 44 for an annular illumination of a macroscope, stereo microscope or macro imaging station. In this context, the combination filter 42 has a concentric arrangement of annular zones, whereas a combination filter 43 has a sequence of alternating, radially aligned zones.

Figure 6:
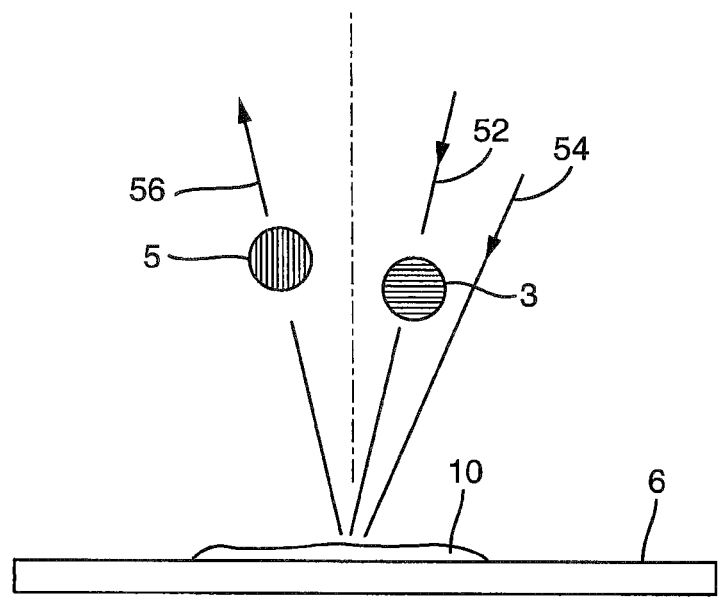
FIG. 6 shows a schematic representation of a further device according to an embodiment of the invention.

FIG. 6 shows a schematic representation of a section of another device in which a specimen 10 is arranged on a specimen carrier 6. This is illuminated with light from two different light sources, namely an internally generated, incident light beam 52 which is polarized by a polarizer 3, and an internally or externally generated colored light beam 52 which is not polarized by the polarizer 3. The light 52 can be monochromatic or narrow band, colored light. The light is reflected by the specimen and proceeds to the analyzer as outgoing light 56.

Figure 7:
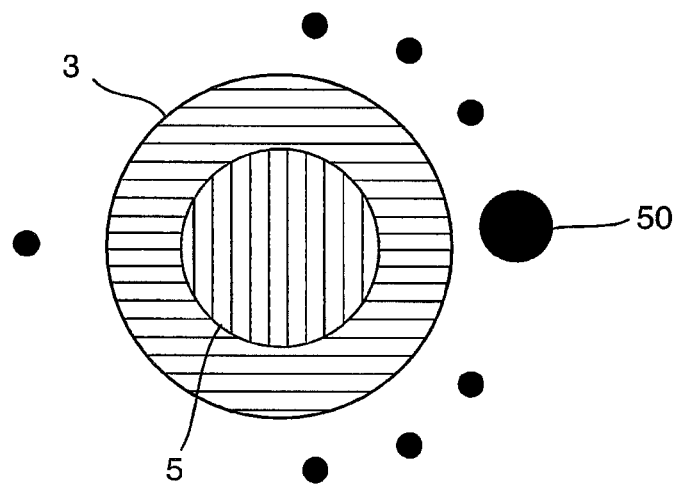
FIG. 7 shows a schematic representation of a further device according to an embodiment of the invention.

FIG. 7 shows this arrangement in the case of a stereo microscope with an Abbé optical system, wherein an inner analyzer 5 is surrounded by a concentric polarizer 3 in the shape of a ring. One or more external, colored light sources 50 are arranged further to the outside. Accordingly, this arrangement functionally corresponds to the one from FIG. 6 in the case of a stereo microscope.

In the cases shown in FIG. 6 and FIG. 7, the result is generated by using two different light sources without requiring color filters which, however, can be part of the internal or external light sources.

The following table lists possible color combinations of perpendicular and parallel, or respectively unpolarized components of the wavelength spectrum which are advantageously possible in the method according to the present disclosure and device according to the present disclosure.

Combined RGB colors are used in this table. Explanation: White=red+green+blue, cyan=green+blue, magenta=red+blue, yellow=red+green.

Embodiments according to the invention can be fulfilled through individual characteristics or a combination of several characteristics. In the scope of the invention, characteristics, which are designated with "in particular" or "preferably" are optional features.

| Components of the illumination light | | RGB components in the image analysis applicable for | |
|---|---|---|---|
| Polarized light | Color-filtered light | Discerning shape | Discerning reflection |
| 1 White | Red | Green + blue | Red |
| 2 White | Green | Red + blue | Green |
| 3 White | Blue | Red + green | Blue |
| 4 White | Cyan | Red | Green + blue |
| 5 White | Magenta | Green | Red + blue |
| 6 White | Amber | Blue | Red + green |
| 7 Cyan | Red | Green + blue | Red |
| 8 Cyan | Amber | Blue | Red + green |
| 9 Cyan | Magenta | Green | Red + blue |
| 10 Magenta | Green | Red + blue | Green |
| 11 Magenta | Amber | Blue | Red + green |
| 12 Magenta | Cyan | Red | Green + blue |
| 13 Amber | Blue | Red + green | Blue |
| 14 Amber | Magenta | Green | Red + blue |
| 15 Amber | Cyan | Red | Green + blue |
| 16 Red | Green | Red | Green |
| 17 Red | Blue | Red | Blue |
| 18 Red | Cyan | Red | Green + blue |
| 19 Green | Red | Green | Red |
| 20 Green | Blue | Green | Blue |
| 21 Green | Magenta | Green | Red + blue |
| 22 Blue | Red | Blue | Red |
| 23 Blue | Green | Blue | Green |
| 24 Blue | Amber | Blue | Red + green |

LIST OF REFERENCE NUMBERS

1 Reflected-light microscope
2 Light house
3 Polarizer
3' Modified polarizer assembly
4 Lenses
5 Analyzer
5' Modified analyzer assembly
6 Specimen carrier
7 Color filter
8 Ocular
9 Imaging device
10 Specimen
11 Reflective particle
13 Non-reflecting particle
20 Coding assembly
21 Incident light
22 Dichroic beam splitter
23, 24 Mirrors
25 Beam recombiner
26 Outgoing light beam
27 First partial beam
28 Second partial beam
30 Coding assembly
31 Incident light
32 Lens
33 Prism
34 Spectral band
35 Combination filter
36 Prism
37 Lens
38 Outgoing light
40, 41 Combination filter
42, 43 Combination filter for stereo microscope
44 Central opening
50 External colored light source
52 Incident light
54 Incident external colored light
56 Outgoing light

What is claimed is:

1. A device for optically determining particle properties, the device comprising:
   at least one light source assembly comprising at least one light source;
   a polarizer assembly;
   at least one sample holder for receiving particle preparations to be analyzed that can be illuminated by the at least one light source assembly;
   at least one analyzer assembly; and
   at least one imaging device comprising at least one color-resolution matrix image sensor,
   wherein the device is configured to direct light reflected by a particle preparation to the at least one color-resolution matrix image sensor by means of color-coded polarization.

2. The device according to claim 1,
   wherein the means for color coding the polarization is configured on the one hand to generate linearly polarized light of at least one first wavelength range in a first polarization direction and, on the other hand, to generate unpolarized light or polarized light with at least one polarization component in a second polarization direction different from the first polarization direction, in at least one second wavelength range, wherein the first wavelength range(s) do not, or only partially, overlap with the second wavelength range(s).

3. The device according to claim 1,
   wherein the first polarization direction is aligned perpendicular to a polarization direction of the at least one analyzer assembly.

4. The device according to one of claim 1,
wherein a coding assembly is included, by means of which the color-coded polarization is generated, and
wherein the coding assembly is a part of the at least one light source assembly, the polarizer assembly or the at least one analyzer assembly.

5. The device according to claim 4,
wherein the coding assembly comprises a dichroic beam splitter which divides incident light into a first partial beam and a second partial beam with different wavelength ranges, wherein a linear polarizer is arranged in the optical path of the first partial beam, and a color filter is arranged in the optical path of the second partial beam, wherein the first partial beam and the second partial beam are combined into an outgoing light beam in a beam recombiner after passing through the linear polarizer or respectively the color filter.

6. The device according to claim 4,
wherein the coding assembly has an arrangement, in the direction of incident light, consisting of a first lens, a first prism, a second prism and a second lens, wherein the incident light is spread out into a spectral band after passing through the first prism, wherein a combination filter with a polarizer and color filter is arranged at the location of the spectral band, by means of which a part of the spectral band is guided through the polarizer, and another part of the spectral band is guided through the color filter.

7. The device according to claim 4,
wherein the coding assembly comprises a combination filter with a pattern having a number of neighboring zones in a linear strip arrangement, a concentric arrangement, or an arrangement with radial strips, wherein the linear polarizers and color filters alternate in neighboring zones.

8. The device according to claim 4,
wherein the coding assembly comprises one or more λ plates that is/are designed to retain the polarization of linearly polarized light at a certain wavelength, and at least partially destroy the polarization at other wavelengths.

9. The device according to claim 1,
wherein at least two different light sources are included, wherein the light sources generate light with at least partially different colors or color spectra.

10. The device according to claim 9,
wherein at least one colored light source is included as an external light source.

11. The device according to claim 1,
wherein the at least one imaging device comprises an image sensor with an upstream Bayer filter, three sensors with a beam splitter prism, and/or upstream color filters, or an X3 color sensor.

12. A method for optically determining particle properties, wherein a particle preparation is placed in a sample holder of a device for optically determining particle properties, in particular according to claim 1, and a color and spatially resolved image of the particle preparation, or a part of the particle preparation, is made, wherein the particle preparation, or a part of the particle preparation, is illuminated in a reflected-light method, wherein light with color-coded polarization reflected by a particle preparation is conducted to at least one matrix image sensor.

13. The method according to claim 12,
wherein the light with color-coded polarization contains on the one hand linearly polarized light of at least one first wavelength range in a first polarization direction and, on the other hand, unpolarized light or polarized light with at least one polarization component in a second polarization direction different from the first polarization direction, in at least one second wavelength range, wherein the first wavelength range(s) do not, or only partially, overlap with the second wavelength range(s).

14. The method according to claim 12,
wherein the light reflected by the particle preparation is conducted through an analyzer with a linear polarization filter, the polarization direction of which is aligned perpendicular to a first polarization direction of the light with color-coded polarization.

15. The method according to claim 12,
wherein size information is determined from the color- and spatially-resolved image information of a single image consisting of at least one wavelength range with a first polarization direction, and information on the reflectivity of particles of the particle preparation is determined from at least one second wavelength range with unpolarized light, or with at least one polarization component, in a second polarization direction different from the first polarization direction.

16. A system for optically determining particle properties, the system comprising:
a device according to claim 1;
an apparatus which has an interface connected to the device,
a data memory; and
a processor for receiving, saving and processing color- and spatially resolved images,
wherein the evaluation apparatus is configured and set up using a computer program to determine size information from the color- and spatially-resolved image information of a single image consisting of at least one wavelength range with a first polarization direction, and to determine information on the reflectivity of particles of the particle preparation from at least one second wavelength range with unpolarized light, or with at least one polarization component, in a second polarization direction different from the first polarization direction.

17. The device according to claim 1, wherein the particle properties are size and reflectivity.

18. The device according to claim 2, wherein the second polarization direction is perpendicular to the first polarization direction.

19. The device according to claim 4, wherein the beam combiner comprises a dichroic beam splitter or a semitransparent mirror.

20. The device according to claim 6, wherein the second prism and the second lens are arranged inverted to the first prism and the first lens with respect to the combination filter.

21. The device according to claim 4, wherein the combination filter has a central opening for an Abbé optical system of a stereo microscope.

22. The device according to claim 1, wherein one light source generates white light, and another light source generates colored light.

23. The method according to claim 12, wherein the particle properties are size and reflectivity.

24. The method according to claim 13, wherein the second polarization direction is perpendicular to the first polarization direction.

25. The system according to claim 16, wherein the particle properties are size and reflectivity.

\* \* \* \* \*